(12) United States Patent
Ghosal et al.

(10) Patent No.: US 12,334,225 B2
(45) Date of Patent: Jun. 17, 2025

(54) SUBPOPULATION BASED PATIENT RISK PREDICTION USING GRAPH ATTENTION NETWORKS

(71) Applicant: SIEMENS HEALTHINEERS AG, Forchheim (DE)

(72) Inventors: Sayan Ghosal, Baltimore, MD (US); Athira Jane Jacob, Plainsboro, NJ (US); Puneet Sharma, Princeton Junction, NJ (US); Mehmet Akif Gulsun, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 417 days.

(21) Appl. No.: 17/647,613

(22) Filed: Jan. 11, 2022

(65) Prior Publication Data
US 2023/0238141 A1 Jul. 27, 2023

(51) Int. Cl.
G16H 50/30 (2018.01)
G16H 50/70 (2018.01)

(52) U.S. Cl.
CPC ............ G16H 50/30 (2018.01); G16H 50/70 (2018.01)

(58) Field of Classification Search
CPC .................................. G16H 50/30; G16H 50/70
See application file for complete search history.

(56) References Cited

U.S. PATENT DOCUMENTS

2022/0367053 A1* 11/2022 Mahmood .............. G16B 40/20

FOREIGN PATENT DOCUMENTS

CN 111261286 A * 6/2020 ............. G16H 10/60

OTHER PUBLICATIONS

Goodwin, Travis, Automatic Generation of a Qualified Medical Knowledge Graph and its Usage for Retrieving Patient Cohorts from Electronic Medical Records, 2013, Semantic Computing (ICSC), 2013 IEEE Seventh International Conference (Year: 2013).*
David Ahmedt-Aristizabal, Graph-Based Deep Learning for Medical Diagnosis and Analysis: Past, Present and Future, Jul. 12, 2021; 21(14):4758. doi: 10.3390/s21144758. PMID: 34300498; PMCID: PMC8309939. (Year: 2021).*
Ahmedt-Aristizabal et al. ( (Year: 2021).*
Khened et al., "Densely Connected Fully Convolutional Network for Short-Axis Cardiac Cine MR Image Segmentation and Heart Diagnosis Using Random Forest," 2018, Statistical Atlases and Computational Models of the Heart. ACDC and MMWHS Challenges, Lecture Notes in Computer Science, vol. 10663, pp. 140-151.
Chen et al., "Using machine learning to predict one-year cardiovascular events in patients with severe dilated cardiomyopathy," 2019, European Journal of Radiology, vol. 117, pp. 178-183.
(Continued)

Primary Examiner — Joshua B Blanchette

(57) ABSTRACT

Systems and methods for graph based assessment of a patient are provided. Medical imaging data and non-imaging medical data of a patient are received. The medical imaging data and the non-imaging medical data are encoded into encoded features using a graph based machine learning network by comparing the patient with patients of a patient population based on a graph of the patient population. An assessment of the patient is determined based on the encoded features using a machine learning classifier network. The assessment of the patient is output.

17 Claims, 6 Drawing Sheets

(56) References Cited

OTHER PUBLICATIONS

Roth et al., "Demographic and Epidemiologic Drivers of Global Cardiovascular Mortality," 2015, The New England Journal of Medicine, vol. 372, pp. 1333-1341.

Veličković et al., "Graph Attention Networks," 2017, eprint arXiv:1710.10903, 12 pgs.

* cited by examiner

SUBPOPULATION BASED PATIENT RISK PREDICTION USING GRAPH ATTENTION NETWORKS

TECHNICAL FIELD

The present invention relates generally to subpopulation based patient risk prediction, and in particular to subpopulation based patient risk prediction using graph attention networks.

BACKGROUND

Cardiovascular diseases are diseases that involve the heart or blood vessels, such as, e.g., coronary artery disease, stroke, heart failure, etc. Early detection of cardiovascular disease has been found to correlate to positive patient outcome. In one conventional approach, cardiovascular disease is detected by extracting features from imaging data and applying a classifier to the extracted features. However, this conventional approach does not consider the clinical health records or the demographic data of the patient. In another conventional approach, imaging and clinical health records are integrated with imaging data to improve classification. However, this conventional approach only considers the patient data of the patient, resulting in reduced generalizability.

BRIEF SUMMARY OF THE INVENTION

In accordance with one or more embodiments, systems and methods for graph based assessment of a patient are provided. Medical imaging data and non-imaging medical data of a patient are received. The medical imaging data and the non-imaging medical data are encoded into encoded features using a graph based machine learning network by comparing the patient with patients of a patient population based on a graph of the patient population. An assessment of the patient is determined based on the encoded features using a machine learning classifier network. The assessment of the patient is output.

In one embodiment, the medical imaging data and the non-imaging medical data are encoded into the encoded features by computing a weighted graph adjacency matrix representing a similarity between the patients of the patient population using one or more graph attention layers of the graph based machine learning network and determining the encoded features based on the weighted graph adjacency matrix. The weighted graph adjacency matrix may be computed based on a measure of dissimilarity between each of the patients in the patient population. The graph comprises nodes each corresponding to one of the patients of the patient population and edges connecting the nodes weighted according to the weighted graph adjacency matrix.

In one embodiment, the medical imaging data is encoded into imaging features using the graph based machine learning network, the non-imaging medical data is encoded into non-imaging features using the graph based machine learning network, and the imaging features and the non-imaging features are concatenated to generate the encoded features. The steps of encoding the medical imaging data into imaging features and encoding the non-imaging medical data into non-imaging features may be performed based on a same weighted graph adjacency matrix.

In one embodiment, determining the assessment of the patient may comprise predicting a risk of cardiovascular disease (or any other disease) or predicting a risk of recurrence of atrial fibrillation after an ablation procedure.

These and other advantages of the invention will be apparent to those of ordinary skill in the art by reference to the following detailed description and the accompanying drawings.

DETAILED DESCRIPTION

The present invention generally relates to methods and systems for subpopulation based patient risk prediction using graph attention networks. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Embodiments described herein provide for the assessment of cardiovascular disease using graph based deep neural networks to integrate imaging and non-imaging patient data of a patient population in a graph. The graph captures population level information for the patient population. Assessment of a respective patient is performed based on a dissimilarity (or similarity) of the respective patient to the patients in the patient population determined using the graph. Advantageously, the graph enables population level information to be exploited for the assessment of each patient, thereby increasing generalizability and improving accuracy and performance.

Figure 1:
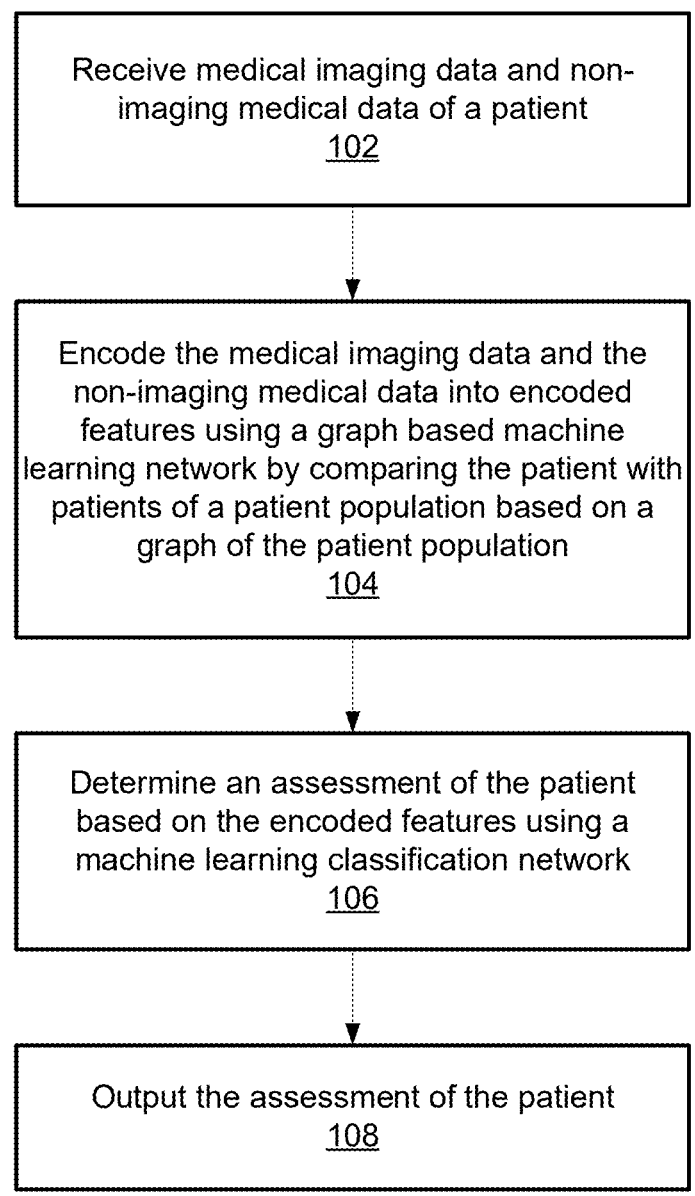
FIG. 1 shows a method for graph based assessment of a patient, in accordance with one or more embodiments.
Figure 2:
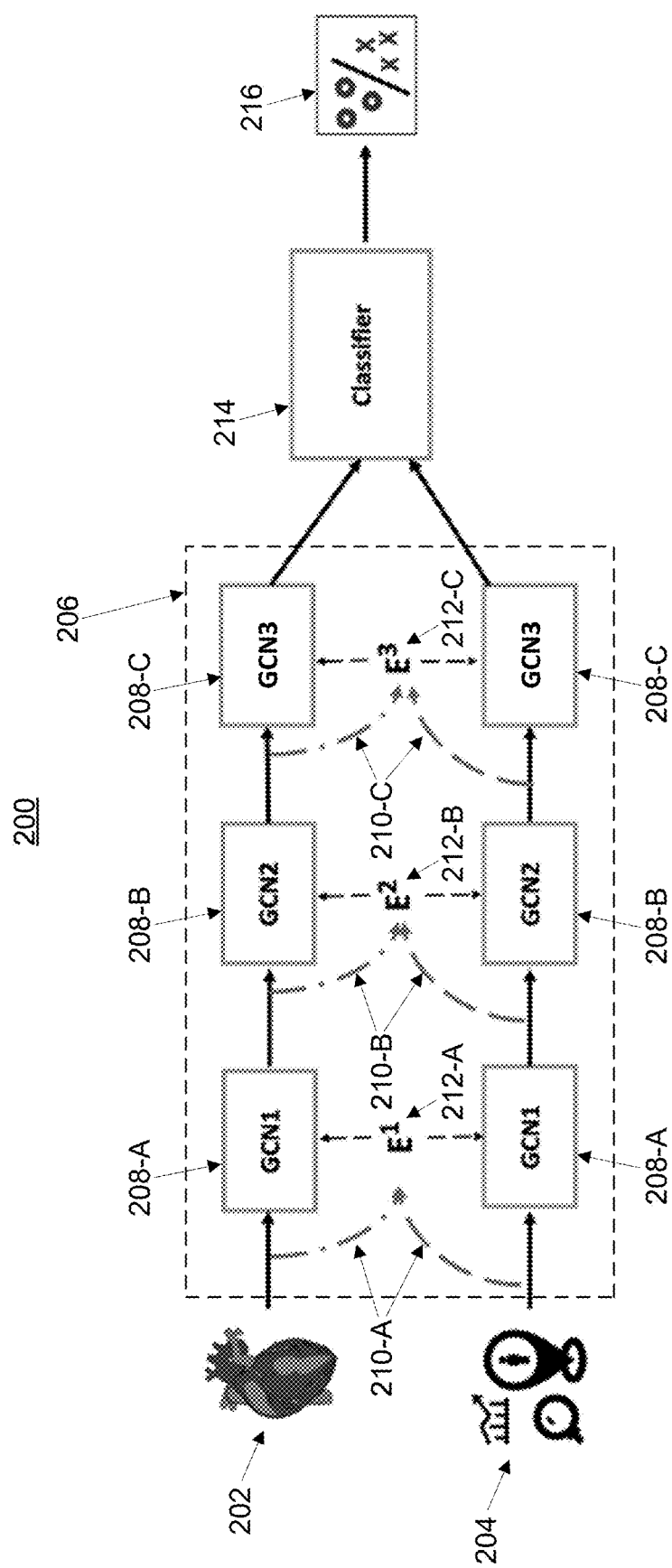
FIG. 2 shows a workflow for graph based assessment of a patient, in accordance with one or more embodiments.

FIG. 1 shows a method 100 for graph based assessment of a patient, in accordance with one or more embodiments. The steps of method 100 may be performed by one or more suitable computing devices, such as, e.g., computer 802 of FIG. 8. FIG. 2 shows a workflow 200 for graph based assessment of a patient, in accordance with one or more embodiments. FIG. 1 and FIG. 2 will be described together.

At step 102 of FIG. 1, medical imaging data and non-imaging medical data of a patient is received. In one example, as shown in FIG. 2, the medical imaging data and the non-imaging medical data is medical imaging data 202 and non-imaging medical data 204 of workflow 200. In one embodiment, the medical imaging data and the non-imaging medical data may comprise data relating to the heart and blood vessels for the assessment of a cardiovascular disease. However, the medical imaging data and the non-imaging medical data may comprise data relating to any other anatomical object of interest for the assessment of that anatomical object of interest.

In one embodiment, the medical imaging data may comprise CT (computed tomography) and/or MRI (magnetic resonance imaging) images of the patient. However, the medical imaging data may comprise images of the patient of any other suitable modality, such as, e.g., US, x-ray, or any other medical imaging modality or combinations of medical imaging modalities. The images of the patient may comprise 2D (two dimensional) images and/or 3D (three dimensional) volumes, and may comprise a single image or a plurality of images.

The non-imaging medical data may comprise any suitable non-imaging medical data of the patient. For example, the non-imaging medical data may comprise medical records, demographic information, etc. of the patient.

The medical imaging data and the non-imaging medical data of the patient can be received by loading such data from a storage or memory of a computer system (such as, e.g., a PACS (picture archiving and communication system), a CHR (clinical health records) database, an EHR (electronic health record) database, etc.) or by receiving such data from a remote computer system. In some embodiments, the medical imaging data may be received directly from an image acquisition device, such as, e.g., a CT scanner, as the imaging data is acquired.

At step 104 of FIG. 1, the medical imaging data and the non-imaging medical data are encoded into encoded features using a graph based machine learning network by comparing the patient with patients of a patient population based on a graph of the patient population. In one example, as shown in FIG. 2, medical imaging data 202 and non-imaging medical data 204 are encoded into encoded features using graph based machine learning network 206. The graph is a representation of the relationship between the patients in the patient population. Each node of the graph represents a patient of the patient population and edges connecting the nodes are weighted according to a weighted adjacency matrix E representing a similarity (or dissimilarity) between patients. The graph is generated by the graph based machine learning network by learning features of each node/patient of the graph and the weight graph adjacency matrix E. The patient may be part of the patient population represented in the graph or may be a new patient being added to the graph.

Formally, the inputs to graph based machine learning network 206 are $\{I_n, J_n\}$, where $I_n$ represents medical imaging data 202 of patient n and $J_n$ represents non-imaging medical data 204 of patient n. Graph based machine learning network 206 comprises one or more graph attention layers 210-A, 210-B, and 210-C (collectively referred to as graph attention layers 210) and one or more GCN (graph convolution) layers 208-A, 208-B, and 208-C (collectively referred to as GCN layers 208). As shown in FIG. 2, graph based machine learning network 206 comprises two branches: one for processing medical imaging data 202 and one for processing non-imaging medical data 204. While each graph attention layer 210 and each GCN layer 208-A, 208-B, and 208-C are separately shown in each of the two branches for processing medical imaging data 202 and non-imaging medical data 204 in workflow 200, it should be understood that each graph attention layer 210 and each GCN layer 208-A, 208-B, and 208-C may be the same graph attention layer or the same GCN layer for processing medical imaging data 202 and non-imaging medical data 204 or different graph attention layers or different GCN layers for processing medical imaging data 202 and non-imaging medical data 204.

GCN layers 208 extract imaging features from medical imaging data 202 and non-imaging features from non-imaging medical data 204 using weighted graph adjacency matrices $E^l$ 212-A, 212-B, and 212-C (collectively referred to as weighted graph adjacency matrices 212), where l is the stage (or layer) of the GCN layers 208. The features of node n at stage l are denoted $I_n^l$, $J_n^l$ for the medical imaging data 202 and the non-imaging medical data 204 respectively. Mathematically, the imaging features $I_n$ of node n at stage l is:

$$I_n^l = \mathcal{N}\left(\sum_{k \in Neighbors(n)} E^l(n,k) I_k^{l-1} W^l + I_n^{l-1} W_s^l\right) \quad \text{(Equation 1)}$$

where $I_n^l$ represent imaging features of node n at stage l extracted from medical imaging data 202, $W^l$ represents the convolution filter weight for stage l, $W_s^l$ represents the convolutional weight for self loop, $E^l(n,k)$ represents the weighted graph adjacency matrix 212 between patient n and patient k for stage l, and $\mathcal{N}(\cdot)$ represents a non-linearity. Equation 1 uses features of its neighbors from previous stages to calculate imaging features $I_n^l$. Equation 1 can be modified to calculate the non-imaging features $J_n$ from non-imaging medical data 204 as follows:

$$J_n^l = \mathcal{N}\left(\sum_{k \in Neighbors(n)} E^l(n,k) J_k^{l-1} W^l + J_n^{l-1} W_s^l\right) \quad \text{(Equation 2)}$$

The weighted graph adjacency matrices $E^l$ 212 are calculated by graph attention layers 210. The weighted graph adjacency matrix $E^l$ 212 is of size N×N, where N is the total number of patients in the patient population. The weighted graph adjacency matrices $E^l$ 212 represent a relationship between patients in the patient population at stage l determined based on a measure of dissimilarity. Mathematically, the weighted graph adjacency matrix $E^l$ 212 is calculated by comparing patient n and patient k as follows:

$$E^l(n,k) = \frac{\exp(-D^l(n,k))}{\sum_{k \in Neighbors(n)} \exp(-D^l(n,k))} \quad \text{(Equation 3)}$$

where $D^l(n,k)$ is a measure of dissimilarity between patient n and patient k.

The measure of dissimilarity $D^l(n,k)$ can be mathematically expressed as:

$$D^l(n,k) = \text{Sim}([f^l(I_n^{l-1}) \| g^l(J_n^{l-1})], [f^l(I_k^{l-1}) \| g^l(J_k^{l-1})]) \quad \text{(Equation 4)}$$

where D(n, k) is a measure of distance between patient n and patient k, Sim(·) is a distance calculating function, and $[f^l(I_n^{l-1}) \| g^l(J_n^{l-1})]$ and $[f^l(I_k^{l-1}) \| g^l(J_k^{l-1})]$ represent the concatenation of the imaging and non-imaging features for patient n and patient k respectively after passing through functions $f^l(\cdot)$ and $g^l(\cdot)$. Sim(·) may be any suitable distance calculating function for measuring the dissimilarity between patient n and patient k. The same weighted graph adjacency matrix $E^l$ 212 is used for encoding both the medical imaging data 202 and the non-imaging medical data 204. This ensures that both the medical imaging data 202 and the non-imaging medical data 204 are encoded in the graph edge weights. The outputs of the last stage of GCN layers 208 (i.e., GCN layer 208-C in workflow 200) are latent features $I_n^{final}$ and $J_n^{final}$ respectively extracted from medical imaging data 202 and non-imaging medical data 204.

It should be understood that graph based machine learning network 206 may be implemented according to any suitable configuration. For example, graph based machine learning network 206 may be implemented with any number of stages (or layers) of the graph attention network 210 and GCN layers 208, with separate or combined branches for processing medical imaging data 202 and non-imaging medical data 204, with shared or separate patient attention weights between different layers, etc.

Figure 3:
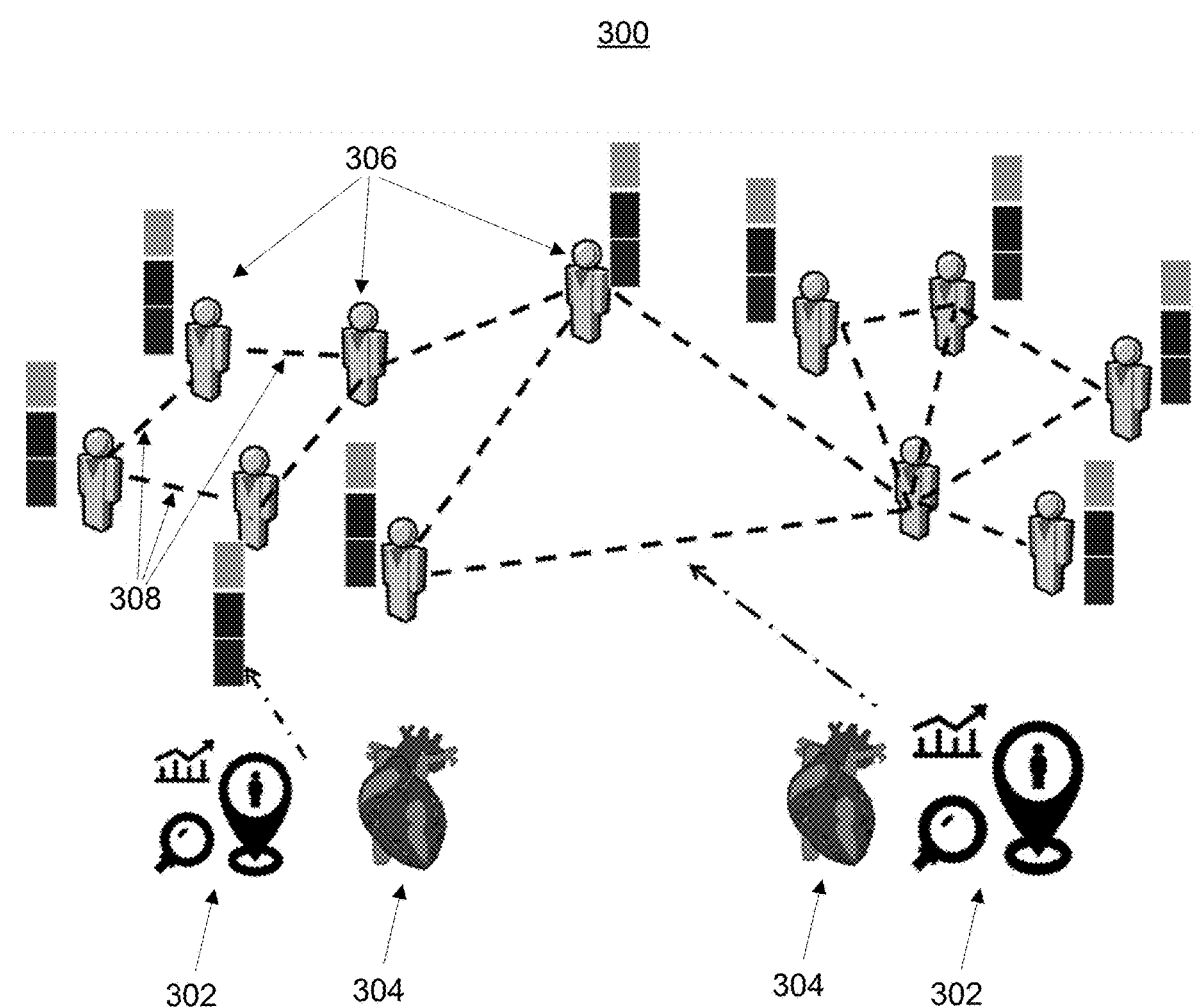
FIG. 3 shows an illustrative graph representing relationships between patients of a patient population, in accordance with one or more embodiments.

FIG. 3 shows an illustrative graph 300 representing relationships between patients of a patient population, in accordance with one or more embodiments. Graph 300 is generated using a graph based machine learning network (e.g., graph based machine learning network 206 of FIG. 2). Graph 300 comprises nodes 306 each representing encoded features of one of the patients of a patient population and edges 308 connecting pairs of nodes 306. Each edge 308 is weighted according to the weighted graph adjacency matrix E to represent the similarity between patients. The extracted features of the patients representing nodes 306 and the weight of edges 308 are determined using the graph based machine learning network based on medical imaging data 304 and non-imaging medical data 302 to generate graph 300.

At step 106 of FIG. 1, an assessment of the patient is determined based on the encoded features using a machine learning classification network. In one example, as shown in FIG. 2, the machine learning classification network is classifier 214 in workflow 200. The machine learning classification network may be any suitable machine learning network for assessing the patient.

Classifier 214 receives as input the encoded features and generates as output the assessment of the patient. In one embodiment, the assessment of the patient comprises a disease diagnosis (e.g., cardiovascular disease). For example, the assessment of the patient may be a predicted risk of cardiovascular disease based on medical imaging data (such as, e.g., coronary CTA (computed tomography angiograph), calcium scoring scans, findings in such scans, etc.) and non-imaging medical data (such as, e.g., clinical health records, patient demographics, lab diagnostics, etc.). In another example, the assessment of the patient may be a predicted risk of recurrence of atrial fibrillation after ablation procedures. However, the assessment of the patient may comprise any other assessment of the patient.

Mathematically, the classification of the node of the patient is predicted as:

$$\hat{y}_n = C(I_n^{final} \| J_n^{final}) \quad \text{(Equation 5)}$$

where $C(\cdot)$ is any suitable classification function and $I_n^{final}$ and $J_n^{final}$ are the concatenated latent encoded features extracted from medical imaging data 202 and non-imaging medical data 204 respectively.

At step 108 of FIG. 1, the assessment of the patient is output. In one example, as shown in FIG. 2, classification 216 is output in workflow 200. For example, the assessment of the patient can be output by displaying the assessment of the patient on a display device of a computer system, storing the assessment of the patient on a memory or storage of a computer system, or by transmitting the assessment of the patient to a remote computer system.

The graph based machine learning network 206 and the classifier 214 are trained during a prior offline or training stage. In one embodiment, graph based machine learning network 206 and the classifier 214 are jointly trained using a cross entropy loss function for class labels from the classifier 214 and a contrastive loss function on the weighted graph adjacency matrices $E^l$ for the graph based machine learning network 206 to enforce similarity between patients of the same class label. This regularizes the frameworks and encourages the model to predict a class label by using information on other patients belonging to the same class. For example, the graph based machine learning network 206 and the classifier 214 may be trained according to the following joint objective loss function:

$$L = \left( -\sum_{n=1}^{N} y_n \log \hat{y}_n + (1 - y_n) \log(1 - \hat{y}_n) \right) + \quad \text{(Equation 6)}$$

$$\left( \lambda \sum_{l=1}^{L} \sum_{i,j}^{all\ pairs} 1_{y_i = y_j} \left( D^l(i, j) \right) + 1_{y_i \neq y_j} \left( 1 - D^l(i, j) \right) \right)$$

where N is the total number of patients in the patient population, $D^l(i, j)$ is a measure of dissimilarity between patient i and patient j, $\lambda$ is a regularization hyperparameter, and L is the total number of convolution layers. The first term is the binary cross entropy loss and the second term is the contrastive loss. The contrastive loss ensures that the encoded features are similar between patients belonging to the same class. During training, the objective loss function of Equation 6 may be minimized using back propagation. Any other suitable loss functions may be applied for training the graph based machine learning network 206 and the classifier 214, such as, e.g., MSE (mean squared error), L1 loss, entropy, etc. Once trained, the trained graph based machine learning network 206 and the trained classifier 214 are applied during an online or inference stage (e.g., during method 100 of FIG. 1).

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 4:
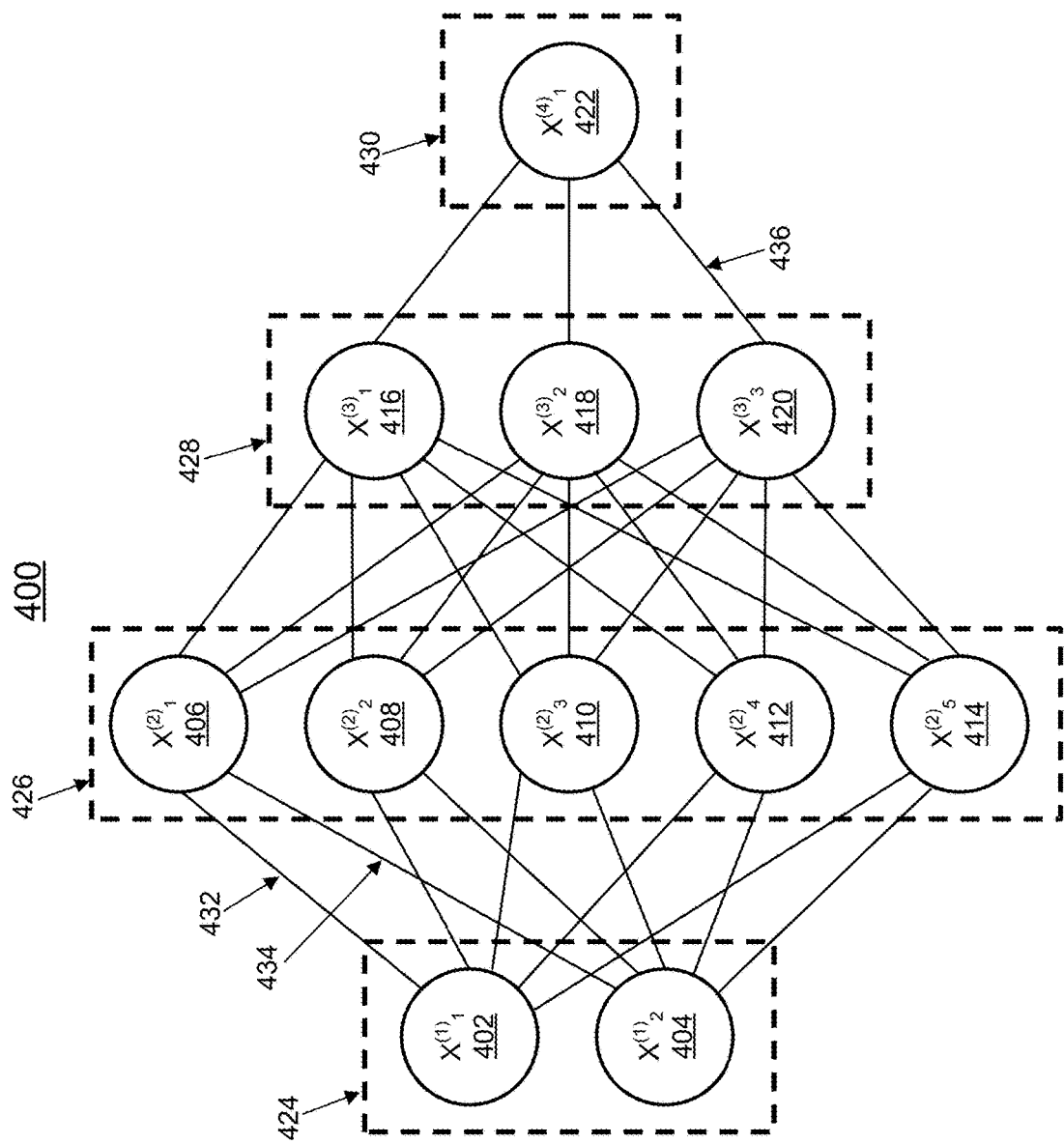
FIG. 4 shows an exemplary artificial neural network that may be used to implement one or more embodiments.

FIG. 4 shows an embodiment of an artificial neural network 400, in accordance with one or more embodiments. Alternative terms for "artificial neural network" are "neural network", "artificial neural net" or "neural net". Machine learning networks described herein, such as, e.g., the graph based machine learning network utilized at step 104 and the machine learning classification network utilized at step 106 of FIG. 1 and the graph based machine learning network 206 comprising GCN layers 208 and graph attention layers 210 and the classifier 214 of FIG. 2, may be implemented using artificial neural network 400.

The artificial neural network 400 comprises nodes 402-422 and edges 432, 434, . . . , 436, wherein each edge 432, 434, . . . , 436 is a directed connection from a first node 402-422 to a second node 402-422. In general, the first node 402-422 and the second node 402-422 are different nodes 402-422, it is also possible that the first node 402-422 and the second node 402-422 are identical. For example, in FIG. 4, the edge 432 is a directed connection from the node 402 to the node 406, and the edge 434 is a directed connection from the node 404 to the node 406. An edge 432, 434, . . . , 436 from a first node 402-422 to a second node 402-422 is also denoted as "ingoing edge" for the second node 402-422 and as "outgoing edge" for the first node 402-422.

In this embodiment, the nodes 402-422 of the artificial neural network 400 can be arranged in layers 424-430, wherein the layers can comprise an intrinsic order introduced by the edges 432, 434, . . . , 436 between the nodes 402-422. In particular, edges 432, 434, . . . , 436 can exist only between neighboring layers of nodes. In the embodiment shown in FIG. 4, there is an input layer 424 comprising only nodes 402 and 404 without an incoming edge, an output layer 430 comprising only node 422 without outgoing edges, and hidden layers 426, 428 in-between the input layer 424 and the output layer 430. In general, the number of hidden layers 426, 428 can be chosen arbitrarily. The number of nodes 402 and 404 within the input layer 424 usually relates to the number of input values of the neural network 400, and the number of nodes 422 within the output layer 430 usually relates to the number of output values of the neural network 400.

In particular, a (real) number can be assigned as a value to every node 402-422 of the neural network 400. Here, x (n); denotes the value of the i-th node 402-422 of the n-th layer 424-430. The values of the nodes 402-422 of the input layer 424 are equivalent to the input values of the neural network 400, the value of the node 422 of the output layer 430 is equivalent to the output value of the neural network 400. Furthermore, each edge 432, 434, . . . , 436 can comprise a weight being a real number, in particular, the weight is a real number within the interval [−1, 1] or within the interval [0, 1]. Here, $w^{(m,n)}_{i,j}$ denotes the weight of the edge between the i-th node 402-422 of the m-th layer 424-430 and the j-th node 402-422 of the n-th layer 424-430. Furthermore, the abbreviation $w^{(n)}_{i,j}$ is defined for the weight $w^{(n,n+1)}_{i,j}$.

In particular, to calculate the output values of the neural network 400, the input values are propagated through the neural network. In particular, the values of the nodes 402-422 of the (n+1)-th layer 424-430 can be calculated based on the values of the nodes 402-422 of the n-th layer 424-430 by $$x_j^{(n+1)}=f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 424 are given by the input of the neural network 400, wherein values of the first hidden layer 426 can be calculated based on the values of the input layer 424 of the neural network, wherein values of the second hidden layer 428 can be calculated based in the values of the first hidden layer 426, etc.

In order to set the values $w^{(m,n)}_{i,j}$ for the edges, the neural network 400 has to be trained using training data. In particular, training data comprises training input data and training output data (denoted as $t_i$). For a training step, the neural network 400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 400 (backpropagation algorithm). In particular, the weights are changed according to $$w'^{(n)}_{i,j}=w^{(n)}_{i,j}-\gamma \cdot \delta_j^{(n)} \cdot x_i^{(n)}$$

wherein γ is a learning rate, and the numbers $\delta^{(n)}_j$ can be recursively calculated as $$\delta_j^{(n)}=(\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)}=(x_k^{(n+1)}-t_j^{(n+1)}) \cdot f'(\Sigma_i x_i^{(n)} \cdot w_{i,j}^{(n)})$$

if the (n+1)-th layer is the output layer 430, wherein f' is the first derivative of the activation function, and $y^{(n+1)}_j$ is the comparison training value for the j-th node of the output layer 430.

Figure 5:
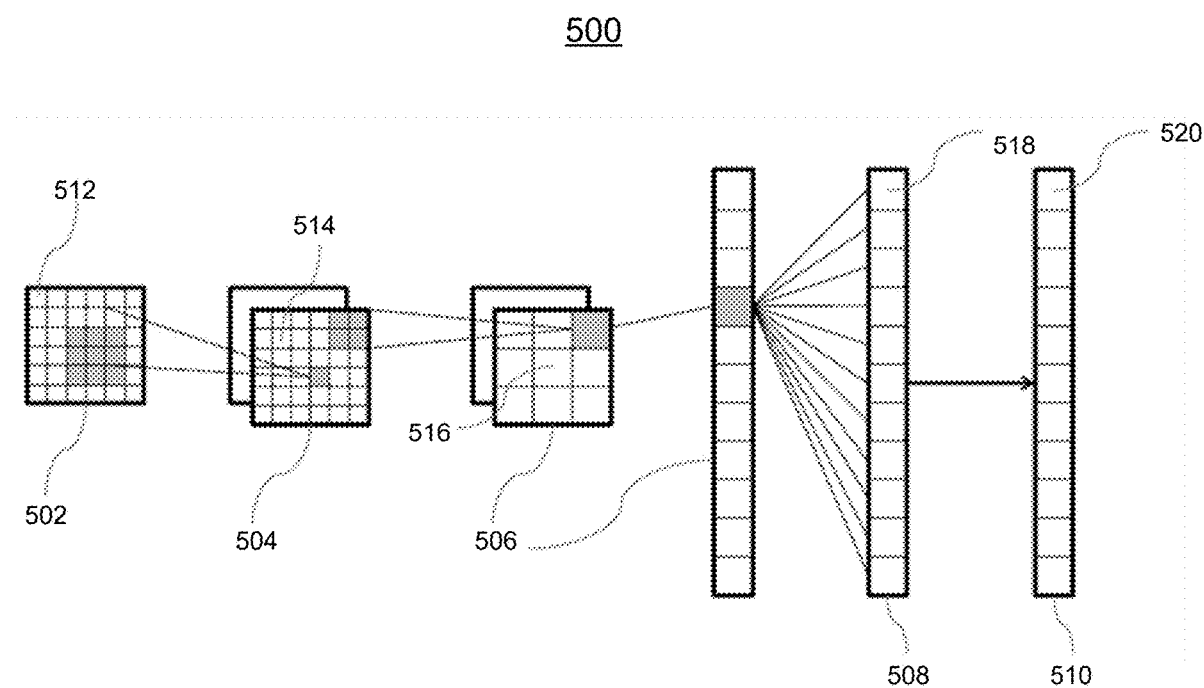
FIG. 5 shows a convolutional neural network that may be used to implement one or more embodiments.

FIG. 5 shows a convolutional neural network 500, in accordance with one or more embodiments. Machine learning networks described herein, such as, e.g., the graph based machine learning network utilized at step 104 and the machine learning classification network utilized at step 106 of FIG. 1 and the graph based machine learning network 206 comprising GCN layers 208 and graph attention layers 210 and the classifier 214 of FIG. 2, may be implemented using convolutional neural network 500.

In the embodiment shown in FIG. 5, the convolutional neural network comprises 500 an input layer 502, a convolutional layer 504, a pooling layer 506, a fully connected layer 508, and an output layer 510. Alternatively, the convolutional neural network 500 can comprise several convolutional layers 504, several pooling layers 506, and several fully connected layers 508, as well as other types of layers. The order of the layers can be chosen arbitrarily, usually fully connected layers 508 are used as the last layers before the output layer 510.

In particular, within a convolutional neural network 500, the nodes 512-520 of one layer 502-510 can be considered to be arranged as a d-dimensional matrix or as a d-dimensional image. In particular, in the two-dimensional case the value of the node 512-520 indexed with i and j in the n-th layer 502-510 can be denoted as $x^{(n)}_{[i,j]}$. However, the arrangement of the nodes 512-520 of one layer 502-510 does not have an effect on the calculations executed within the convolutional neural network 500 as such, since these are given solely by the structure and the weights of the edges.

In particular, a convolutional layer 504 is characterized by the structure and the weights of the incoming edges forming a convolution operation based on a certain number of kernels. In particular, the structure and the weights of the incoming edges are chosen such that the values $x^{(n)}_k$ of the nodes 514 of the convolutional layer 504 are calculated as a convolution $x^{(n)}_k = K_k * x^{(n-1)}$ based on the values $x^{(n-1)}$ of the nodes 512 of the preceding layer 502, where the convolution * is defined in the two-dimensional case as $$x_k^{(n)[i,j]} = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 512-518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 512-520 in the respective layer 502-510. In particular, for a convolutional layer 504, the number of nodes 514 in the convolutional layer is equivalent to the number of nodes 512 in the preceding layer 502 multiplied with the number of kernels.

If the nodes 512 of the preceding layer 502 are arranged as a d-dimensional matrix, using a plurality of kernels can be interpreted as adding a further dimension (denoted as "depth" dimension), so that the nodes 514 of the convolutional layer 504 are arranged as a (d+1)-dimensional matrix. If the nodes 512 of the preceding layer 502 are already arranged as a (d+1)-dimensional matrix comprising a depth dimension, using a plurality of kernels can be interpreted as expanding along the depth dimension, so that the nodes 514 of the convolutional layer 504 are arranged also as a (d+1)-dimensional matrix, wherein the size of the (d+1)-dimensional matrix with respect to the depth dimension is by a factor of the number of kernels larger than in the preceding layer 502.

The advantage of using convolutional layers 504 is that spatially local correlation of the input data can exploited by enforcing a local connectivity pattern between nodes of adjacent layers, in particular by each node being connected to only a small region of the nodes of the preceding layer.

In embodiment shown in FIG. 5, the input layer 502 comprises 36 nodes 512, arranged as a two-dimensional 6×6 matrix. The convolutional layer 504 comprises 72 nodes 514, arranged as two two-dimensional 6×6 matrices, each of the two matrices being the result of a convolution of the values of the input layer with a kernel. Equivalently, the nodes 514 of the convolutional layer 504 can be interpreted as arranges as a three-dimensional 6×6×2 matrix, wherein the last dimension is the depth dimension.

A pooling layer 506 can be characterized by the structure and the weights of the incoming edges and the activation function of its nodes 516 forming a pooling operation based on a non-linear pooling function f. For example, in the two dimensional case the values $x^{(n)}$ of the nodes 516 of the pooling layer 506 can be calculated based on the values $x^{(n-1)}$ of the nodes 514 of the preceding layer 504 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 506, the number of nodes 514, 516 can be reduced, by replacing a number d1·d2 of neighboring nodes 514 in the preceding layer 504 with a single node 516 being calculated as a function of the values of said number of neighboring nodes in the pooling layer. In particular, the pooling function f can be the max-function, the average or the L2-Norm. In particular, for a pooling layer 506 the weights of the incoming edges are fixed and are not modified by training.

The advantage of using a pooling layer 506 is that the number of nodes 514, 516 and the number of parameters is reduced. This leads to the amount of computation in the network being reduced and to a control of overfitting.

In the embodiment shown in FIG. 5, the pooling layer 506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 508 can be characterized by the fact that a majority, in particular, all edges between nodes 516 of the previous layer 506 and the nodes 518 of the fully-connected layer 508 are present, and wherein the weight of each of the edges can be adjusted individually.

In this embodiment, the nodes 516 of the preceding layer 506 of the fully-connected layer 508 are displayed both as two-dimensional matrices, and additionally as non-related nodes (indicated as a line of nodes, wherein the number of nodes was reduced for a better presentability). In this embodiment, the number of nodes 518 in the fully connected layer 508 is equal to the number of nodes 516 in the preceding layer 506. Alternatively, the number of nodes 516, 518 can differ.

Furthermore, in this embodiment, the values of the nodes 520 of the output layer 510 are determined by applying the Softmax function onto the values of the nodes 518 of the preceding layer 508. By applying the Softmax function, the sum the values of all nodes 520 of the output layer 510 is 1, and all values of all nodes 520 of the output layer are real numbers between 0 and 1.

A convolutional neural network 500 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 500 can be trained based on the backpropagation algorithm. For preventing overfitting, methods of regularization can be used, e.g. dropout of nodes 512-520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
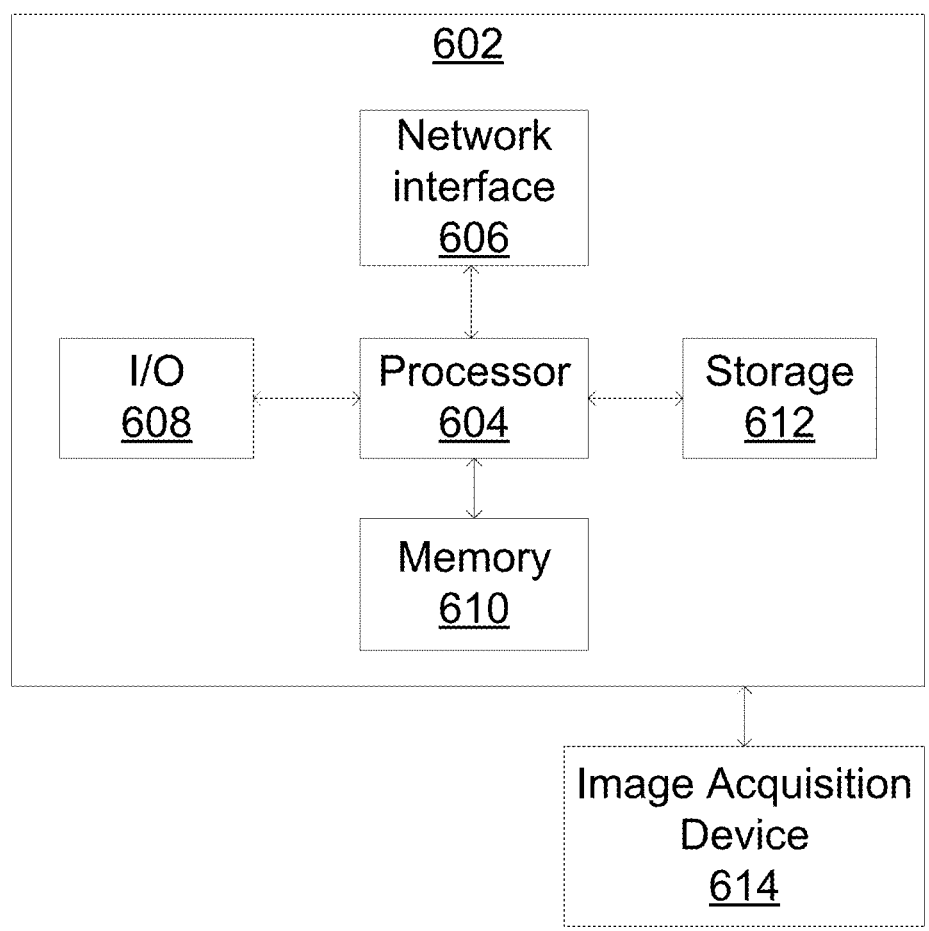
FIG. 6 shows a high-level block diagram of a computer that may be used to implement one or more embodiments.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIG. 1 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIG. 1. Accordingly, by executing the computer program instructions, the processor 604 executes the method and workflow steps or functions of FIG. 1. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 communicate wirelessly through a network. In a possible embodiment, the computer 602 can be located remotely with respect to the image acquisition device 614.

Any or all of the systems and apparatus discussed herein may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method for an improved assessment of a patient using a graph based machine learning network, the method comprising:
receiving medical imaging data and non-imaging medical data of a patient;
encoding the medical imaging data and the non-imaging medical data into encoded features using a graph based machine learning network having a plurality of stages, the graph based machine learning network comprising a graph attention layer and a graph convolution layer at each of the plurality of stages, each of the graph attention layers determining a weighted graph adjacency matrix by comparing the patient with patients of a patient population, and each of the graph convolution layers extracting features from the medical imaging data and the non-imaging medical data using the weighted graph adjacency matrix determined by the graph attention layer at the same one of the plurality of stages to generate the encoded features, wherein the graph attention layers at one or more of the plurality of stages determine the weighted graph adjacency matrices based on the features extracted by the graph convolution layers at a previous one of the one or more stages;
determining an assessment of the patient based on the encoded features using a machine learning classifier network; and
outputting the assessment of the patient.

2. The computer-implemented method of claim 1, wherein comparing the patient with patients of a patient population comprises:
determining a measure of dissimilarity between the patient and the patients in the patient population.

3. The computer-implemented method of claim 1, wherein the graph based machine learning network generates a graph comprising nodes each corresponding to one of the patients of the patient population and edges connecting the nodes weighted according to the weighted graph adjacency matrices.

4. The computer-implemented method of claim 1, wherein encoding the medical imaging data and the non-imaging medical data into encoded features using a graph based machine learning network comprises:
encoding the medical imaging data into imaging features using the graph based machine learning network;
encoding the non-imaging medical data into non-imaging features using the graph based machine learning network; and
concatenating the imaging features and the non-imaging features to generate the encoded features.

5. The computer-implemented method of claim 4, wherein the steps of encoding the medical imaging data into imaging features and encoding the non-imaging medical data into non-imaging features are performed based on a same weighted graph adjacency matrix.

6. The computer-implemented method of claim 1, wherein determining an assessment of the patient based on the encoded features using a machine learning classifier network comprises:
predicting a risk of cardiovascular disease.

7. The computer-implemented method of claim 1, wherein determining an assessment of the patient based on the encoded features using a machine learning classifier network comprises:
predicting a risk of recurrence of atrial fibrillation after an ablation procedure.

8. An apparatus for an improved assessment of a patient using a graph based machine learning network, the apparatus comprising:
means for receiving medical imaging data and non-imaging medical data of a patient;
means for encoding the medical imaging data and the non-imaging medical data into encoded features using a graph based machine learning network having a plurality of stages, the graph based machine learning network comprising a graph attention layer and a graph convolution layer at each of the plurality of stages, each of the graph attention layers determining a weighted graph adjacency matrix by comparing the patient with patients of a patient population, and each of the graph convolution layers extracting features from the medical imaging data and the non-imaging medical data using the weighted graph adjacency matrix determined by the graph attention layer at the same one of the plurality of stages to generate the encoded features, wherein the graph attention layers at one or more of the plurality of stages determine the weighted graph adjacency matrices based on the features extracted by the graph convolution layers at a previous one of the one or more stages;

means for determining an assessment of the patient based on the encoded features using a machine learning classifier network; and means for outputting the assessment of the patient.

9. The apparatus of claim 8, wherein comparing the patient with patients of a patient population comprises:

determining a measure of dissimilarity between the patient and the patients in the patient population.

10. The apparatus of claim 8, wherein the graph based machine learning network generates a graph comprising nodes each corresponding to one of the patients of the patient population and edges connecting the nodes weighted according to the weighted graph adjacency matrices.

11. The apparatus of claim 8, wherein the means for encoding the medical imaging data and the non-imaging medical data into encoded features using a graph based machine learning network comprises:

means for encoding the medical imaging data into imaging features using the graph based machine learning network;

means for encoding the non-imaging medical data into non-imaging features using the graph based machine learning network; and means for concatenating the imaging features and the non-imaging features to generate the encoded features.

12. The apparatus of claim 11, wherein the steps of encoding the medical imaging data into imaging features and encoding the non-imaging medical data into non-imaging features are performed based on a same weighted graph adjacency matrix.

13. A non-transitory computer readable medium storing computer program instructions for an improved assessment of a patient using a graph based machine learning network, the computer program instructions when executed by a processor cause the processor to perform operations comprising:

receiving medical imaging data and non-imaging medical data of a patient;

encoding the medical imaging data and the non-imaging medical data into encoded features using a graph based machine learning network having a plurality of stages, the graph based machine learning network comprising a graph attention layer and a graph convolution layer at each of the plurality of stages, each of the graph attention layers determining a weighted graph adjacency matrix by comparing the patient with patients of a patient population, and each of the graph convolution layers extracting features from the medical imaging data and the non-imaging medical data using the weighted graph adjacency matrix determined by the graph attention layer at the same one of the plurality of stages to generate the encoded features, wherein the graph attention layers at one or more of the plurality of stages determine the weighted graph adjacency matrices based on the features extracted by the graph convolution layers at a previous one of the one or more stages;

determining an assessment of the patient based on the encoded features using a machine learning classifier network; and outputting the assessment of the patient.

14. The non-transitory computer readable medium of claim 13, wherein comparing the patient with patients of a patient population comprises:

determining a measure of dissimilarity between the patient and the patients in the patient population.

15. The non-transitory computer readable medium of claim 13, wherein the graph based machine learning network generates a graph comprising nodes each corresponding to one of the patients of the patient population and edges connecting the nodes weighted according to the weighted graph adjacency matrices.

16. The non-transitory computer readable medium of claim 13, wherein determining an assessment of the patient based on the encoded features using a machine learning classifier network comprises:

predicting a risk of cardiovascular disease.

17. The non-transitory computer readable medium of claim 13, wherein determining an assessment of the patient based on the encoded features using a machine learning classifier network comprises:

predicting a risk of recurrence of atrial fibrillation after an ablation procedure.

* * * * *